US009062288B2

(12) United States Patent
Vesey

(10) Patent No.: US 9,062,288 B2
(45) Date of Patent: Jun. 23, 2015

(54) THERAPEUTIC METHODS USING ADIPOSE TISSUE-DERIVED CELL SUSPENSIONS COMPRISING ADIPOCYTES

(75) Inventor: Graham Vesey, Gordon (AU)

(73) Assignee: Regeneus LTD, Gordon (AU)

( * ) Notice: Subject to any disclaimer, the term of this patent is extended or adjusted under 35 U.S.C. 154(b) by 618 days.

(21) Appl. No.: 13/059,646

(22) PCT Filed: Aug. 20, 2009

(86) PCT No.: PCT/AU2009/001070
§ 371 (c)(1),
(2), (4) Date: Jul. 28, 2011

(87) PCT Pub. No.: WO2010/020005
PCT Pub. Date: Feb. 25, 2010

(65) Prior Publication Data
US 2011/0293577 A1    Dec. 1, 2011

(30) Foreign Application Priority Data

Aug. 22, 2008  (AU) ............................... 2008904326
May 14, 2009  (AU) ............................... 2009201915

(51) Int. Cl.
*A61K 35/35*    (2015.01)
*C12N 5/077*    (2010.01)
*A61K 35/12*    (2015.01)

(52) U.S. Cl.
CPC ............... *C12N 5/0653* (2013.01); *A61K 35/12* (2013.01); *A61K 35/35* (2013.01)

(58) Field of Classification Search
None
See application file for complete search history.

(56) References Cited

U.S. PATENT DOCUMENTS

| | | | |
|---|---|---|---|
| 5,688,531 | A | 11/1997 | Benayahu et al. |
| 5,837,235 | A | 11/1998 | Mueller et al. |
| 6,429,013 | B1 | 8/2002 | Halvorsen et al. |
| 7,534,451 | B2 | 5/2009 | Erbe et al. |
| 2003/0054331 | A1 | 3/2003 | Fraser et al. |
| 2004/0259190 | A1 | 12/2004 | Naughton |
| 2005/0048036 | A1 | 3/2005 | Hendrick et al. |
| 2005/0153441 | A1 | 7/2005 | Hendrick et al. |
| 2006/0018887 | A1* | 1/2006 | Kadiyala et al. ............ 424/93.7 |
| 2006/0140914 | A1 | 6/2006 | Jain et al. |
| 2006/0228796 | A1* | 10/2006 | Kolkin et al. ................ 435/325 |
| 2007/0036768 | A1* | 2/2007 | Fraser et al. ................ 424/93.7 |
| 2008/0318317 | A1 | 12/2008 | Roche et al. |
| 2010/0015200 | A1* | 1/2010 | McClain et al. ............. 424/423 |
| 2011/0268708 | A1 | 11/2011 | Lin |
| 2012/0308533 | A1* | 12/2012 | Imanishi et al. ............ 424/93.7 |
| 2013/0164267 | A1* | 6/2013 | Lin et al. .................... 424/93.7 |

FOREIGN PATENT DOCUMENTS

| | | |
|---|---|---|
| AU | 200035223 B2 | 9/2009 |
| AU | 2009201915 B1 | 9/2009 |
| WO | 9836704 A1 | 8/1998 |
| WO | 0053795 A1 | 9/2000 |
| WO | 0132129 A2 | 5/2001 |
| WO | 03022988 A3 | 3/2003 |
| WO | 03024215 A1 | 3/2003 |
| WO | 03053346 A2 | 7/2003 |
| WO | 03080801 A2 | 10/2003 |
| WO | 03085099 A2 | 10/2003 |
| WO | 2005013885 A2 | 2/2005 |
| WO | 2005035738 A1 | 4/2005 |
| WO | 2005035742 A2 | 4/2005 |
| WO | 2005042730 A2 | 5/2005 |
| WO | 2005095581 A1 | 10/2005 |
| WO | 2005113780 A1 | 12/2005 |
| WO | 2006121445 A2 | 11/2006 |
| WO | 2007011644 A3 | 1/2007 |
| WO | 2007016112 A2 | 2/2007 |
| WO | 2007034115 A1 | 3/2007 |
| WO | 2007039150 A2 | 4/2007 |
| WO | 2007065927 A1 | 6/2007 |
| WO | 2007086637 A1 | 9/2007 |
| WO | 2007103442 A1 | 9/2007 |
| WO | 2007145442 A1 | 12/2007 |
| WO | 2008155659 A2 | 12/2008 |

OTHER PUBLICATIONS

Hu et al, Mol Biol Rep, 2011, vol. 38, pp. 873-878.*
Chen et al, Biochim Biophys Acta, 2006, vol. 1762, pp. 711-718.*
Stofkova et al, Endocrin Regul, 2009, vol. 43, pp. 157-168.*
Almehed, K. et al., "Role of resistin as a marker of inflammation in systemic lupus erythematous," 2008, Arthritis Research and Therapy, 10:R15.
Aplin, A. C., et al., "Angiopoietin-1 and vascular endothelial growth factor induce expression of inflammatory cytokines before angiogenesis," 2006, Physiol Genomics,27:20-28.
Bandyopadhyay, G. et al., "Glucose Activates Protein Kinease C-ζ/λ through Proline-rich Tyrosine Kinase-2, Extracellular Signal-Regulated Kinase and Phospholipase D. A Novel Mechanism for Activating Glucose Transporter Translocation," 2001,The Journal of Biological Chemistry, 276:35537-35545.
Bennett, J, H., et al. "Adipocytic cells cultured from marrow have osteogenic potential," 1991,Journal of Cell Science, 99:131-139.
Bieback, K. et al., "Human Alternatives to Fetal Bovine Serum for the Expansion of Mesenchymal Stromal Cells from Bone Marrow," 2009, Stem Cells, 27:2331-2341.

(Continued)

*Primary Examiner* — Allison Fox
(74) *Attorney, Agent, or Firm* — McDonnell Boehnen Hulbert & Bergoff LLP

(57) ABSTRACT

Provided herein is a use of an adipose tissue-derived cell suspension which comprises adipocytes for the preparation of a pharmaceutical composition for use in the treatment of an inflammatory disorder, a cartilage or bone disorder and/or the alleviation of pain associated with an inflammatory disorder in a mammalian subject. Also provided herein is a method of treating an inflammatory disorder, a cartilage or bone disorder or alleviating pain associated with an inflammatory disorder in a mammalian subject, comprising administering to the subject a pharmaceutical composition which comprises: (i) an adipose tissue-derived cell suspension which comprises adipocytes; or (ii) a cell-free extract which is prepared from an adipose tissue-derived cell suspension, wherein the adipose tissue-derived cell suspension comprises adipocytes, together with a pharmaceutically-acceptable carrier or diluent.

7 Claims, No Drawings

(56) References Cited

OTHER PUBLICATIONS

Blaber, S.P., et al., "Analysis of in vitro secretion profiles from adipose-derived cell populations," 2012, Journal of Translation Medicine, 10:172.

Black, L. L., et al., "Effect of Adipose-Derived Mensenchymal Stem and Regenerative Cells on Lameness in Dogs with Chronic Osteoarthritis of the Coxofemoral Joints: A Randomized, Double-Blinded, Multicenter, Controlled Trial," 2007, Veterinary Therapeutics, 8:272-284.

Castellot, J. J., et al., "Potent stimulation of vascular endothelial cell growth by differentiated 3T3 adipocytes," 1980, Proceeding of the National Academy of Science USA, 77:6007-6011.

Castellot, J. J., et al., "Differentiation-dependent stimulation of neovascularization and endothelial cells chemotaxis by 3T3 adipocytes," 1982, Proceedings of the National Academy of Science USA, 79:5597-5601.

Considine, R. V., et al., "Paracrine stimulation of preadipocyte-enriched cell cultures by mature adipocytes," 1996, Endocrinol Metab, 33:E895-E899.

Cross, D. A. E. et al., "Insulin activates protein Kinase B, inhibits glycogen synthase kinase-3 and activates glycogen synthase by rapamycin-insensitive pathways in skeletal muscle and adipose tissue," 1997, FEBS Letters, 406:211-215.

Ehling, A., et al., "The Potential of Aiponectin in Driving Arthritis," 2008, The Journal of Immunology, 176:4468-4478.

Gale, N. W., et al., "Complementary and Coordinated Roles of the VEGFs and Angiopoietins during Normal and Pathologic Vascular Formation," 2002,Cold Spring Harb Symp Quant Biol, 27:267-274.

Gesta, S. et al., "Evidence for a role of developmental genes in the origin of obesity and body fat distribution," 2006, Proceedings of the National Academy of Science, 103:6676-6681.

Gimble, J. M., et al., "Adipose-Derived Stem Cells for Regenerative Medicine," 2007, Circulation Research, 100:1249-1260.

Gordon, D. et al., "Human mesenchymal stem cells abrogate experimental allergic encephalomyelitis after intraperitoneal injection, and with sparse CNS infiltration," 2008, Neuroscience Letters, 448:71-73.

Helder, M. N., et al., "Stem Cells from Adipose Tissue Allow Challenging New Concepts for Regenerative Medicine," 2007, Tissue Engineering, 00:1-10.

Juge-Aubry, C. E., et al., "Adipose tissue is a major source of interleukin-1 receptor antagonist," 2003, Diabetes, 52:1104-1110.

Juge-Aubry, C. E., et al., "Adipose tissue is a regulated source of interleukin-10," 2005, Cytokine, 29:270-274.

Khachigian, L. M. "Collagen antibody-induced arthritis," 2006, Nature Protocols, 1:2512-2516.

Kim, J.-M., et al., "Systemic transplantation of human adipose stem cells attenuated cerebral inflammation and degeneration in a haemorrhagic stroke model," 2007, Brain Research, 1183:43-50.

Kim, W.-S., et al., "Wound healing effect of adipose-derived stem cells: A critical role of secretory factors on human dermal fibroblasts," 2007, Journal of Dermatological Science, 48:15-24.

Lee, S.-W., et al., "Adiponectin mitigates the severity of arthritis in mice with collagen-induced arthritis," 2008, Scandinavian Rheumatology Research Foundation, 38:260-268.

Lee, J. H., et al., "A Novel Approach to Adipocyte Analysis," 2012, Plastic and Reconstructive Surgery,129:380-387.

Leonhardt, W., et al., "Human Adipocyte Volumes: Maximum Size, and Correlation to Weight Index in Maturity Onset-Diabetes" 1972, Dibetologia, 8:287-291.

Leonhardt, W., et al., "The adipocyte volume in human adipose tissue: 1. Lipid space, normal and maximum values, and the relation to body weight index," 1978, International Journal of Obesity, 2:33-45.

Long, D. A. et al. "Angiopoietin-1 therapy enhances fibrosis and inflammation following folic acid-induced acute renal injury," 2008, Kidney International, 74:300-309.

Maruotti, N. et al., "Angiogenesis in rheumatoid arthritis," 2006, Histol Histopathol, 21:557-566.

McDonald, K., "Dog days for adult stem cells," 2009, Australian Life Scientist, March/April: 62 and 65.

Moreno-Navarrete, J., M. And Fernandez-Real, J. M., "Chapter 2 Adipocyte Differentiation," 2012, Adipose Tissue Biology, Springer Science & Business Media, LLC 2012. pp. 17-38.

Nakagami, H., et al., "Adipose Tissue-Derived Stromal Cells as a Novel Option for Regenerative Cell Therapy," 2006, Journal of Atherosclerosis and Thrombosis, 13:77-81.

Nambu, M. et al, Abstract Y1-3 "Development of Refractory Ulcer Treatment with Adipose Tissue-Derived Cells," 2008 Wound Repair and Regeneration, The 36th Annual Meeting of the Japanese Society for Wound Healing, Jan.-Feb. 16: A1-A9.

Oksenberg, D., et al., "A Single amino-acid difference confers major pharmacological variation between human and rodent 5-HT1B receptors," 1992, Nature, 360:161-163.

Ouchi, N. et al., "Adipokines in inflammation and metabolic disease," 2011, Nat Rev Immunol., 11:85-97.

Pajvani, U., et al., "Structure-Function Studies of the Adipocyte-secreted Hormone Acrp30/Adiponectin," 2008, The Journal of Biological Chemistry, 278:9073-9085.

Park, S. R., et al., "Interconversion potential of cloned human marrow adipocytes in vitro," 1999, Bone, 24:549-554.

Piasecki, J. H. et al., "An experimental model for improving fat graft viability and purity," 2007, Plastic and Reconstructive Surgery, 119:1571-1583.

Piasecki, J.H., et al., "Purified viable fat suspended in matrigel improves longevity," 2008, Asthetic Surgery Journal, 28:24-32.

Puissant, B., et al., "Immunomodulatory effect of human adipose tissue-derived adult stem cells: comparison with bone marrow mensenchymal stem cells," 2005, British Journal of Haematology, 129:118-129.

Rehman, J. et al., "Secretion of Angiogenic and Antiapoptotic Factors by Human Adipose Stromal Cells," 2004, Circulation,109:1292-1298.

Rosen, E. D. and MacDougald, O. A., "Adipocyte differentiation from the inside out," 2006, Nature Reviews: Molecular Cell Biology, 7:885-896.

Schaffler, A., "Concise Review: Adipose Tissue-Derived Stromal Cells—Basic and clinical Implications for Novel Cellased Therapies," 2007, Stem Cells, 25:818-827.

Schaffler, A., et al., "Role of Adipose Tissue as an Inflammatory Organ in Human Diseases," 2006, Endocrine Reviews, 27:449-467.

Skurk, T. et al., "The proatherogenic cytokine interleukin-18 is secreted by human adipocytes," 2005, European Journal of Endocrinology, 152:863-868.

Sonoda, et al., "A New Organotypic Culture of Adipose Tissue Fragments Maintains Viable Mature Adipocytes for a Long Term, Together with Development of Immature Adipocytes and Mensenchymal stem Cell-Like Cells," 2008, Endocrinology, 149:4795-4798.

Sugihara, H., et al., "Effects of fat cells on keratinocytes and fibroblasts in a reconstructed rat skin model using collagen gel matrix culture," 2001, British Journal of Dermatology,144:244-253.

Sumi, et al.,"Transplantation of adipose stromal cells, but not mature adipocytes, augments ischemia-induced angiogenesis," 2007, Life Sciences, 80:559-565.

Szekanecz, Z. and Koch, A. E., "Mechanisms of Disease: angiogenesis in inflammatory diseases," 2007, Nat Clin Pract Rheumatol, 3:635-643.

Tanti, J. F. et al., "Overexpression of a constitutively active form of phosphatidylinositol 3-Kinase is sufficient to promote glut 4 translocation in adipocytes," 1996, The Journal of Biological Chemistry, 271:25227-25232.

Wolf, A. M., et al., "Adiponectin induces the anti-inflammatory cytokines IL-10 and IL-1RA in human leukocytes," 2004 Biochemical and Biophysical Research Communications, 323:630-635.

Yanez, R., et al., "Adipose Tissue-Derived Mensenchymal Stem Cells Have in Vivo Immunosuppressive Properties Applicable for the Control of the Graft-Versus-Host Disease," 2006, Stem Cells, 24:2582-2591.

Yoshimura, A. et al., "Cellular and molecular basis for the regulation of inflammation by TGF-β," 2010, J. Biochem, vol. 147:781-792.

Zheng, X. et al., "Proteomic Analysis for the Assessment of Different Lots of Fetal Bovine Serum as a Raw Material for Cell Culture. Part IV. Application of Proteomics to the Manufacture of Biological Drugs," 2006, Biotechnol. Prog., vol. 22:1294-1300.

* cited by examiner

US 9,062,288 B2

THERAPEUTIC METHODS USING ADIPOSE TISSUE-DERIVED CELL SUSPENSIONS COMPRISING ADIPOCYTES

RELATED APPLICATIONS

The present application is a U.S. national phase application under 35 U.S.C. §371 of International Patent Application No. PCT/AU2009/001070, filed Aug. 20, 2009, which claims benefit from Australian provisional patent application No. 2008904326 entitled "Therapeutic Methods" filed Aug. 22, 2008 and Australian patent application No. 2009201915 entitled "Therapeutic Methods" filed May 14, 2009, the entire contents of each of which are incorporated herein by reference.

TECHNICAL FIELD

The present invention relates to the use of an adipose-derived cell suspension for the preparation of a pharmaceutical composition for the treatment of an inflammatory disorder and/or the alleviation of pain which is associated with an inflammatory disorder, and to methods of treating an inflammatory disorder and/or alleviating pain associated with an inflammatory disorder using such pharmaceutical compositions.

BACKGROUND OF THE INVENTION

Adipose tissue contains a cell population of large, lipid-filled adipocytes and a population of non-adipocyte cells, which comprises cells associated with various connective fibres and cells associated with capillaries and larger blood vessels. The non-adipocyte cell population also comprises a variety of infiltrating immune cells and cells and cell processes associated with the nervous system. The non-adipocyte cell population is also thought to comprise a population of adipose-derived adult stem cells and consequently there has been interest in using adipose tissue as a source of isolated adult stem cells for various therapeutic applications.

In general, methods for obtaining adipose tissue-derived presumptive adult stem cells involves depleting adipocytes from adipose-derived non-adipocyte cells, which requires digesting adipose tissue with enzymes such as collagenase, and then separating the liberated cells by centrifuging the digested sample. During centrifugation, the adipose-derived non-adipocyte cells separate from the adipocytes to form a pellet, whereas the lipid containing adipocytes float. The fraction containing the non-adipocyte cells is then used as a source of tissue stem cells.

SUMMARY OF THE INVENTION

In a first aspect there is provided the use of an adipose tissue-derived cell suspension which comprises adipocytes for the preparation of a pharmaceutical composition for use in the treatment of an inflammatory disorder or the alleviation of pain associated with an inflammatory disorder in a subject.

In a second aspect there is provided the use of an adipose tissue-derived cell suspension which comprises adipocytes for the preparation of a pharmaceutical composition for use in the treatment of a cartilage or bone disorder in a subject.

In a third aspect there is provided a method of treating an inflammatory disorder or a cartilage or bone disorder, or alleviating pain associated with an inflammatory disorder in a subject, comprising administering to the subject a pharmaceutical composition which comprises:
  (i) an adipose tissue-derived cell suspension which comprises adipocytes; or
  (ii) a cell-free extract which is prepared from an adipose tissue-derived cell suspension, wherein the adipose tissue-derived cell suspension comprises adipocytes,
together with a pharmaceutically-acceptable carrier or diluent.

In certain embodiments the adipose tissue-derived cell suspension is freshly isolated.

In certain embodiments, the pharmaceutical composition is a cell free extract.

In certain embodiments the adipose tissue-derived cell suspension is autologous to the subject. In other embodiments, the adipose tissue-derived cell suspension is allogeneic to the subject.

In certain embodiments the subject is a human. In certain embodiments the pharmaceutical composition is a veterinary composition and the subject is a non-human mammal, such as a canine or feline subject.

In certain embodiments, the inflammatory disorder is selected from a joint-related inflammatory disorder, corneal inflammation, skin inflammation or inflammation associated with wounding. In certain embodiments the inflammatory disorder is a skin or corneal ulcer.

In certain embodiments the cartilage or bone disorder is a cartilage or bone fracture, for instance a non-union bone fracture, or osteoporosis.

In another aspect there is provided a pharmaceutical composition which comprises:
  (i) an adipose tissue-derived cell suspension which comprises adipocytes; or
  (ii) a cell-free extract which is prepared from an adipose tissue-derived cell suspension, wherein the adipose tissue-derived cell suspension comprises adipocytes,
together with a pharmaceutically-acceptable carrier or diluent.

In another aspect there is provided a method of generating an adipose tissue-derived cell suspension which comprises adipocytes from a sample of adipose tissue from a mammal, the method comprising:
  dissociating the sample of adipose tissue to form a suspension of cells which comprises adipocytes;
  centrifuging the suspension of cells to form a cell pellet, a floating cell layer which comprises adipocytes and an intermediate layer which is depleted of cells relative to the cell pellet and the floating cell layer; and
  removing the intermediate layer and mixing the cell pellet and floating cell layer to form an adipose tissue derived cell suspension which comprises adipocytes.

In certain embodiments of this method, the adipose tissue-derived cell suspension which comprises adipocytes is generated from the sample of adipose tissue within 6 hours of the sample of adipose tissue being obtained from the mammal.

ABBREVIATIONS

DMEM Dulbecco's Modified Eagles Medium
RPMI Roswell Park Memorial Institute Medium

DETAILED DESCRIPTION OF THE PREFERRED EMBODIMENTS

Described herein are compositions comprising adipose tissue-derived cell suspensions which retain at least a substantial portion of the adipocyte fraction, and use of these compositions for treating inflammatory disorders, cartilage or bone disorders or for alleviating pain associated with inflammatory disorders. Without wishing to be bound by any proposed mechanism of action, it is proposed that adipocytes and/or interactions between adipocytes and adipose-derived non-adipocyte cells may contribute to therapeutic activity of an adipose-tissue derived cell suspension for treating inflammatory disorders, cartilage or bone disorders or for alleviating pain associated with inflammatory disorders.

Accordingly, in a first aspect there is provided the use of an adipose tissue-derived cell suspension which comprises adipocytes for the preparation of a pharmaceutical composition for use in the treatment of an inflammatory disorder or the alleviation of pain associated with an inflammatory disorder in a subject.

In a second aspect there is provided the use of an adipose tissue-derived cell suspension which comprises adipocytes for the preparation of a pharmaceutical composition for use in the treatment of a cartilage or bone disorder in a subject.

In a third aspect there is provided a method of treating an inflammatory disorder or a cartilage or bone disorder or alleviating pain associated with an inflammatory disorder in a subject, comprising administering to the subject a pharmaceutical composition which comprises:
 (i) an adipose tissue-derived cell suspension which comprises adipocytes; or
 (ii) a cell-free extract which is prepared from an adipose tissue-derived cell suspension, wherein the adipose tissue-derived cell suspension comprises adipocytes,
together with a pharmaceutically-acceptable carrier or diluent.

Adipose Tissue

Adipose tissue may be human adipose tissue or mammalian animal adipose tissue. The human or animal may be alive or dead, but preferably provided that there are still is viable adipocyte cells within the adipose tissue. The adipose tissue may be derived from a mature animal or from a juvenile animal. In particular embodiments the animal is a companion animal, such as a canine or a feline domestic animal, or a working animal. In other particular embodiments the mammal is a farm animal, stud animal, or racing animal such as equines (including horses, donkeys, asses), bovines (including cattle and buffaloes), ovines, caprines, porcines, and camelids (including camels, llamas, alpacas and the like). In other embodiments the animal is a research animal, such as a rodent. In other embodiments the animal is a zoo animal, such as a member of the family Felidae, a member of the family Canidae, a member of the order Rodentia, or a member of the one of the orders of Cetacea, Perissodactyla, Artiodactyla, Tubulidentata, Hyracoidea, Sirenia, or Proboscidea.

The adipose tissue may originate from the same individual subject in which the pharmaceutical composition will be administered, in which the adipose tissue-derived cell suspension is autologous. The adipose tissue may originate from a different individual of the same species to the subject in which the pharmaceutical composition will be administered, in which case the adipose tissue-derived cell suspension is allogeneic. In certain embodiments the adipose tissue may originate from an individual of a different species to the subject in which the pharmaceutical composition will be administered, in which the adipose tissue-derived cell suspension is xenogeneic.

The adipose tissue may originate from any source in the body which is accessible. Subcutaneous fat, for example, is readily accessible with only superficial wounding, or by using keyhole surgery techniques. Subcutaneous adipose tissue may be collected using liposuction techniques. Adipose tissue for may, for example, be removed with reproductive tissue when de-sexing a male or female mammal. The adipose tissue may comprise "white" adipose tissue and/or "brown" adipose tissue. In particular embodiments the adipose tissue comprises white adipose tissue only.

The adipose tissue may be rinsed with a tissue culture medium or buffered isotonic solution to remove adherent red blood cells, and may be trimmed or coarsely processed to remove large blood vessels or connective tissue elements prior to generating an adipose tissue-derived cell suspension.

Adipose Tissue-Derived Cell Suspension

The term "adipose tissue-derived cell suspension" as used herein encompasses isolated cells from adipose tissue or small aggregates or pieces of adipose tissue, or a mixture of two or more of isolated cells, small aggregates and pieces of adipose tissue.

The cell suspension may be obtained by mechanically dissociating adipose tissue using techniques which are readily available in the art. Any suitable method for the mechanical dissociation of adipose tissue may be used, for example by mincing adipose tissue with blades, or with scissors, or by forcing adipose tissue through screens or meshes with a pore size sufficient to break the tissue into isolated cells and/or small pieces of adipose tissue. A combination of suitable techniques may be used. Small aggregates of adipose tissue may form when dissociated adipose-derived cells reassociate into larger assemblies, for example on standing in a medium. Small pieces or aggregates of adipose tissue may be less than ten millimeters in maximum diameter, less than five millimeters in maximum diameter, less than one millimeter in maximum diameter, less than 500 µm in maximum diameter or less than 250 µm in maximum diameter. In certain embodiments, a mechanical dissociation technique is used without using one or more proteolytic enzymes. The techniques employed in these embodiments may be used to rapidly generate an adipose tissue-derived cell suspension.

The adipose tissue-derived cell suspension may be filtered through a mesh or screen to remove cell aggregates or tissue pieces which are greater than the mesh or screen pore size.

In certain embodiments, proteolytic enzymes are used to promote the dissociation of adipose tissue into an adipose tissue-derived cell suspension. Enzymes which are suitable for such a use are well known in the art, and include but are not limited to trypsin, and collagenase. It is usual to remove and/or otherwise inactivate the proteolytic enzymes before using the adipose tissue-derived cell suspension, as these enzymes may not be compatible with a desired in vivo use of the cell suspension. In certain embodiments, proteolytic enzymes in combination with techniques for the mechanical dissociation of adipose tissue are used to generate an adipose tissue-derived cell suspension.

In particular embodiments the cell suspension may be suspended in a medium. The medium may be added to the adipose tissue before, during or after the dissociation of the adipose tissue. The medium may be a medium which is capable of maintaining adipose tissue cell survival for at least 24 hours under appropriate culture conditions, such as a tissue culture medium. The medium may be an isotonic buffered solution, such as a phosphate or a HEPES buffered saline, which is capable of maintaining adipose tissue cell survival for at least one hour. The medium may be a serum free medium. The medium may comprise serum or serum components which support or extend adipose tissue cell survival in the cell suspension. The serum or serum components may be autologous serum or serum components. The serum or serum components may be allogeneic serum or serum components from a single individual or pooled from multiple individuals.

In a further embodiment the cell suspension is not suspended in a medium, but instead the cells are suspended in liquid which is formed during the dissociation of the tissue.

In certain embodiments the preparation of an adipose tissue-derived cell suspension comprises a centrifugation step. The centrifugation of isolated cells or small aggregates or pieces of adipose tissue suspended in a liquid, such as a medium, is at approximately 500 g for 10 minutes, or for sufficient time and at a sufficient g-force to generate a cell pellet which comprises adipose-derived non-adipocyte cells, above which is a layer of medium, floating above which in turn is a layer which comprises adipocytes, and floating at the top is a layer of lipid which is derived from ruptured adipocytes. Following centrifugation, in certain embodiments the lipid layer and the medium layer is discarded and the retained cells are mixed, leaving an adipose tissue-derived cell suspension which comprises adipocytes and adipose-derived non-adipocyte cells.

In certain embodiments multiple centrifugation steps may be used, for example to provide additional cell separation steps.

In other embodiments, the preparation of an adipose tissue-derived cell suspension does not include a centrifugation step.

The adipose tissue-derived cell suspension may be freshly isolated, that is administered to the recipient within approximately 6 hours of the removal of the fat tissue from the donor. Alternatively, the adipose tissue-derived cell suspension may be stored for more than 6 hours, typically when suspended in a medium, prior to administration to a recipient.

The adipose tissue-derived cell suspension comprises adipocytes. In particular embodiments the adipocytes comprise viable adipocytes. In particular embodiments, the adipocytes retain detectable quantities of lipid in their cytoplasm, and may be separated from adipose-derived non-adipocyte cells on the basis of the different density provided by the lipid. Lipid may be detectable using light microscopy techniques, including phase contrast microscopy, or by staining a sample of cells with a lipophilic dye such as Oil Red O. Adipocytes which retain lipid in their cytoplasm are considerably more fragile than other adipose-derived cells and accordingly, where viable adipocytes are required, techniques for dissociating tissue or storing a cell suspension which damage or render non-viable a large proportion of the adipocytes should be avoided. The ultrasonic dissociation of adipose tissue or techniques in which adipose tissue is vigorously shaken, for example, are unlikely to provide a cell suspension which contains large numbers of viable adipocytes. The viability of adipocytes may readily be determined using readily available techniques, such as the LIVE/DEAD cell viability assays (Molecular Probes).

In certain embodiments, the adipose tissue-derived cell suspension does not comprise substantial numbers of adipose-derived non-adipocyte cells. In these embodiments, the adipose tissue-derived cell suspension may be conveniently prepared by methods which comprise a centrifugation step, as described herein, by which the pelleted adipose-derived non-adipocyte cells are excluded.

In certain embodiments, the adipose tissue-derived cell suspension is depleted of CD34 immunoreactive cells, or of cells which are adherent to a tissue culture plastic substratum following incubation at 37° C. overnight in a serum-containing medium. CD34 immunoreactive cells may be selected and depleted on the basis of their expression of CD34 on their plasma membranes, using for example immunoaffinity methods, such as magnetic bead cell separation methods or fluorescence activated cell sorting methods. Antibodies which are specific for CD34 and which are suitable for immunoaffinity methods are commercially available for humans and a range of animals including dogs, cats, rats, mice, cows and sheep, from Becton Dickinson (San Jose, USA), Invitrogen, Beckman Coulter (Miami, USA), AbD Serotec (Oxford, UK) and VMRD (Pullman, Wash., USA). The depletion of CD34 immunoreactive cells may be a complete depletion (ie a removal of 100% of immunoreactive cells which were present in the cell suspension prior to depletion) or it may be a partial depletion, in which case a proportion of CD34 immunoreactive cells are removed. The depletion may involve a removal of at least 50%, at least 60%, at least 70%, at least 80%, or at least 90% of CD34 immunoreactive cells.

In certain embodiments, the adipose tissue-derived cell suspension comprises both adipocytes and adipose-derived non-adipocyte cells. In these embodiments, the adipose tissue-derived cell suspension may be conveniently prepared by methods which comprise a centrifugation step, as described herein, in which both the adipocyte cell layer and the pelleted adipose-derived non-adipocyte cells are collected. Alternatively, in these embodiments the adipose tissue-derived cell suspension may be prepared by dissociating adipose tissue as described herein without a centrifugation step.

Pharmaceutical Compositions

In certain aspects the adipose tissue-derived cell suspension which comprises viable adipocytes is used for the preparation of a pharmaceutical composition.

In certain embodiments of these aspects, the pharmaceutical composition comprises the adipose tissue-derived cell suspension and a pharmaceutically acceptable carrier or diluent. In these embodiments, the adipose tissue derived cell suspension may be freshly isolated from adipose tissue obtained from a subject, for example by mechanical dissociation of adipose tissue as described herein, and mixed with a pharmaceutically acceptable carrier or diluent to produce a pharmaceutical composition suitable for administration back to the subject, without exposing the adipose tissue-derived cell suspension to a medium for a prolonged period.

Alternatively, the pharmaceutical composition may comprise an adipose tissue-derived cell suspension which has been held in a medium or has been held in a viable or non-viable form frozen in cryostorage medium. The cells from the cell suspension may be harvested from the medium or the cryostorage medium and combined with a pharmaceutically acceptable carrier or diluent when needed for the preparation of the pharmaceutical composition. Cells may be harvested from a medium by centrifugation, or by filtration using readily available techniques known in the art.

In other embodiments, the pharmaceutical composition comprises a cell-free extract which is generated by exposure of a medium to the adipose tissue-derived cell suspension which comprises adipocytes. Exposure of the medium to the adipocyte tissue-derived cell suspension does not require conditions which enable cell attachment to a substratum. In these embodiments, the cell-free extract may be generated by exposing a medium to the adipose tissue-derived cell suspension for at least 6 hours, at least 8 hours, at least 10 hours, or at least 12 hours followed by removal of the cell suspension from the medium, for example by centrifugation or by filtration. In certain embodiments the cell free extract is generated by exposing a medium to the adipose tissue-derived cell suspension for no more than 12 hours, no more than 18 hours or no more than 24 hours. The cell-free extract may comprise cell-derived molecules which are released from cells following cell death or the breakup of adipose tissue cells. The cell-free extract may comprise secretions of cells of the adipose tissue-derived cell suspension. The exposing of a medium to an adipose tissue-derived cell suspension may be at a temperature of from 4° C. to 50° C., more typically at a temperature of from 10° C. to 40° C. and most typically at a temperature of from 20° C. to 37° C.

For a typical adipose tissue-derived cell suspension, 10 g of adipose tissue is dissociated and suspended in 20 mls of DMEM containing 10% autologous serum. The adipose tissue derived cell suspension typically comprises from 100,000 to 1,000,000 non-adipocyte cells for every gram of adipose tissue source material. The number of adipocytes per gram of adipose tissue source material is typically between 100,000 and 5,000,000.

The term "medium" as used herein is intended to encompass compositions which support the survival of at least some cells in an adipose tissue-derived cell suspension for at least one hour. The medium may be a tissue culture medium, such as DMEM, RPMI, or minimal essential medium, optionally supplemented with serum. The medium may be a buffered isotonic solution, such as a phosphate buffered saline or Hank's buffered saline solution, provided the medium is suitable for administration to a subject. The medium may be liquid which is formed during the dissociation of adipose tissue. The medium may optionally be supplemented with factors which promote cell survival or attachment and cell division, such as insulin, progesterone and selenium, or serum or serum components. In certain embodiments the medium must be suitable for a pharmaceutical composition, which is acceptable for in vivo use. Such a medium will be substantially free of pyrogens or other impurities which may be harmful to humans or animals. Pharmaceutically-acceptable media are commercially available. The phrase "pharmaceutically acceptable" refers to molecular entities and compositions that do not produce adverse, allergic, or other untoward reactions when administered to an animal or a human.

In certain embodiments of the second aspect, the pharmaceutical composition comprises the adipose tissue-derived cell suspension which comprises adipocytes or a cell-free extract generated by an adipose tissue-derived cell suspension which comprises adipocytes as described above. Typically the pharmaceutical composition also comprises a pharmaceutically acceptable carrier or diluent.

In certain embodiments of either the first or second aspects, the adipose tissue is taken from an individual subject, if serum supplementation is used for the cell suspension then the serum is derived from the same individual, and the pharmaceutical composition is administered to the same individual, and thus the adipose tissue-derived cell suspension is an autologous composition. In this embodiment the pharmaceutical composition may comprise the adipose tissue-derived cell suspension or a cell free extract.

In certain embodiments, the adipose tissue is taken from one or more individual is subjects and the pharmaceutical composition is administered to a different subject of the same species, and thus the adipose tissue-derived cell suspension is an allogeneic cell suspension. In these embodiments the pharmaceutical composition may, but need not necessarily, comprise a cell free extract rather than a cell suspension so as to minimise the possibility of host immune responses to the pharmaceutical composition or graft versus host disease, where the adipose-derived cell suspension comprises cells of the immune system.

In certain embodiments the pharmaceutical composition is pooled from multiple adipose tissue-derived cell suspensions. These may either be pooled from different preparations taken from the same individual or from different preparations taken from different individuals.

In certain embodiments the pharmaceutical composition of the first and second aspects may be administered directly to the site of inflammation, or to the site of bone or cartilage damage, or to the site where the pain is experienced. For example, where the inflammatory disorder is a joint-related inflammatory disorder, the pharmaceutical composition may be administered directly into the synovial fluid and/or into or around the joint capsule, and/or into the musculature overlying or surrounding the joint, and/or subcutaneously to the tissue overlying the joint. The quantity of pharmaceutical composition which may be administered will depend on the size and location of the joint, and the site of administration. Where administration is by injection into the synovial fluid of a joint, for example, the volume may be constrained by the volume of the synovial fluid which is held at the joint.

Typically joint-related inflammatory disorders in humans involve at least one joint in one or both hips, knees, ankles, elbows, shoulders, wrists, the metacarpo-phalangeal articulations or the phalangeal articulations, the metatarso-tarsal articulations or the tarsal articulations or between two or more vertebrae. For veterinary joint-related inflammatory disorders the corresponding joints are involved in mammalian animals, and these include the stifle and hock joints.

Where the pharmaceutical composition is locally administered, the pharmaceutical composition may comprise an adipose tissue-derived cell suspension and/or a cell free extract generated by exposure of a medium to an adipose tissue-derived cell suspension which comprises adipocytes.

Where the pharmaceutical composition is administered locally for a cartilage or bone disorder, adipose tissue-derived cell suspensions or cell-free extracts may be suspended in viscous-forming biologically tolerated solution, such as a collagen, alginate, fibrin, hyaline, plasma or Matrigel™ solution, prior to administration at the site of cartilage or bone damage or where bone or cartilage repair is needed. Cells or cell-free extracts may also be loaded onto permanent or degradable biocompatible matrices, such as polylactic and/or polyglycolic acid matrices or demineralised bone matrices. Methods for the administration of cells for use in cartilage or bone repair are described in U.S. Pat. No. 7,078,232 entitled "Adipose tissue-derived adult stem or stromal cells for the repair of articular cartilage fractures and uses thereof" (Konkle and Gimble), the entire contents of which is incorporated herein by reference.

The pharmaceutical composition may be administered to the skin topically, or via subcutaneous injection, intraepidermal injection, or via transdermal delivery, systems for which are available in the art. Typically a transdermal delivery system will comprise the pharmaceutical composition formulated with one or more agents which increase the permeability of the skin to the composition.

Where the pharmaceutical composition is administered topically, for example for the treatment of skin inflammation, it may be formulated in an aqueous based cream or lotion, such as a cetomacrogol cream or a sorbolene cream to increase residency at the skin surface.

Where the pharmaceutical composition is administered to the cornea, it may be formulated with an oil-based ointment which is acceptable for corneal administration, or it may be admixed with corneally-acceptable artificial tear solutions which increase residency time at the corneal surface. Corneal administration may also be prolonged through the use of a corneal depot, such as a contact lens which has been soaked in the pharmaceutical composition.

In other embodiments the pharmaceutical composition of these aspects may be administered systemically, for example where the inflammatory disorder is diffuse such as over large areas of skin, or where deep internal organs are involved. Systemic administration may involve intravenous administration of the pharmaceutical composition, or intraperitoneal administration. Typically, but not necessarily exclusively, where administration is intravenous, a cell-free extract generated by exposure of a medium to an adipose tissue-derived cell suspension which comprises adipocytes is used, to reduce the possibility of causing a lipid embolism. The present studies have, however, demonstrated that intravenous injections of adipose-derived cell suspensions comprising adipocytes are tolerated for example in animal subjects.

In other embodiments local or systemic administration may be by direct injection or via a slow release pump or depot.

Inflammatory Disorders

The pharmaceutical composition may be administered for the treatment of an inflammatory disorder and/or for alleviating pain associated with an inflammatory disorder in a subject.

Inflammation may arise as a response to an injury or abnormal stimulation caused by a physical, chemical, or biologic agent. An inflammation reaction may include the local reactions and resulting morphologic changes, destruction or removal of injurious material such as an infective organism, and responses that lead to repair and healing. The term "inflammatory" when used in reference to a disorder refers to a pathological process which is caused by, resulting from, or resulting in inflammation that is inappropriate or which does not resolve in the normal manner. Inflammatory disorders may be systemic or localized to particular tissues or organs.

Inflammation is known to occur in many disorders which include, but are not limited to: Systemic Inflammatory Response (SIRS); Alzheimer's Disease (and associated conditions and symptoms including: chronic neuroinflammation, glial activation; increased microglia; neuritic plaque formation; Amyotrophic Lateral Sclerosis (ALS), arthritis (and associated conditions and symptoms including, but not limited to: acute joint inflammation, antigen-induced arthritis, arthritis associated with chronic lymphocytic thyroiditis, collagen-induced arthritis, juvenile arthritis, rheumatoid arthritis, osteoarthritis, prognosis and streptococcus-induced arthritis, spondyloarthropathies, and gouty arthritis), asthma (and associated conditions and symptoms, including: bronchial asthma; chronic obstructive airway disease, chronic obstructive pulmonary disease, juvenile asthma and occupational asthma); cardiovascular diseases (and associated conditions and symptoms, including atherosclerosis, autoimmune myocarditis, chronic cardiac hypoxia, congestive heart failure, coronary artery disease, cardiomyopathy and cardiac cell dysfunction, including: aortic smooth muscle cell activation, cardiac cell apoptosis and immunomodulation of cardiac cell function); diabetes (and associated conditions, including autoimmune diabetes, insulin-dependent (Type 1) diabetes, diabetic periodontitis, diabetic retinopathy, and diabetic nephropathy); gastrointestinal inflammations (and related conditions and symptoms, including celiac disease, associated osteopenia, chronic colitis, Crohn's disease, inflammatory bowel disease and ulcerative colitis); gastric ulcers; hepatic inflammations such as viral and other types of hepatitis, cholesterol gallstones and hepatic fibrosis; HIV infection (and associated conditions, including degenerative responses, neurodegenerative responses, and HIV associated Hodgkin's Disease); Kawasaki's Syndrome (and associated diseases and conditions, including mucocutaneous lymph node syndrome, cervical lymphadenopathy, coronary artery lesions, edema, fever, increased leukocytes, mild anemia, skin peeling, rash, conjunctiva redness, thrombocytosis); nephropathies (and associated diseases and conditions, including diabetic nephropathy, endstage renal disease, acute and chronic glomerulonephritis, acute and chronic interstitial nephritis, lupus nephritis, Goodpasture's syndrome, hemodialysis survival and renal ischemic reperfusion injury); neurodegenerative diseases or neuropathological conditions (and associated diseases and conditions, including acute neurodegeneration, induction of IL-I in aging and neurodegenerative disease, IL-I induced plasticity of hypothalamic neurons and chronic stress hyperresponsiveness, myelopathy); ophthalmopathies (and associated diseases and conditions, including diabetic retinopathy, Graves' ophthalmopathy, inflammation associated with corneal injury or infection including corneal ulceration, and uveitis), osteoporosis (and associated diseases and conditions, including alveolar, femoral, radial, vertebral or wrist bone loss or fracture incidence, postmenopausal bone loss, fracture incidence or rate of bone loss); otitis media (adult or paediatric); pancreatitis or pancreatic acinitis; periodontal disease (and associated diseases and conditions, including adult, early onset and diabetic); pulmonary diseases, including chronic lung disease, chronic sinusitis, hyaline membrane disease, hypoxia and pulmonary disease in SIDS; restenosis of coronary or other vascular grafts; rheumatism including rheumatoid arthritis, rheumatic Aschoff bodies, rheumatic diseases and rheumatic myocarditis; thyroiditis including chronic lymphocytic thyroiditis; urinary tract infections including chronic prostatitis, chronic pelvic pain syndrome and urolithiasis; immunological disorders, including autoimmune diseases, such as alopecia aerata, autoimmune myocarditis, Graves' disease, Graves ophthalmopathy, lichen sclerosis, multiple sclerosis, psoriasis, systemic lupus erythematosus, systemic sclerosis, thyroid diseases (e.g. goitre and struma lymphomatosa (Hashimoto's thyroiditis, lymphadenoid goitre); lung injury (acute hemorrhagic lung injury, Goodpasture's syndrome, acute ischemic reperfusion), myocardial dysfunction, caused by occupational and environmental pollutants (e.g. susceptibility to toxic oil syndrome silicosis), radiation trauma, and efficiency of wound healing responses (e.g. burn or thermal wounds, chronic wounds, surgical wounds and spinal cord injuries), septicaemia, acute phase response (e.g. febrile response), general inflammatory response, is acute respiratory distress response, acute systemic inflammatory response, wound healing, adhesion, immuno-inflammatory response, neuroendocrine response, fever development and resistance, acute-phase response, stress response, disease susceptibility, repetitive motion stress, tennis elbow, and pain management and response.

In particular embodiments the inflammatory disorder is selected from joint-related inflammatory disorders, corneal inflammation, skin inflammation or wound healing.

In particular embodiments the joint-related inflammatory disorder is arthritis.

Cartilage or Bone Disorders

The pharmaceutical composition may be administered for the treatment of a cartilage or bone disorder in a subject. It may be administered for the treatment of a combination of a cartilage and a bone disorder, for example where a fracture involves both bone and cartilage. A cartilage or bone disorder may include a fracture of cartilage, a fracture of bone, such as a traumatic fracture of cartilage or bone. A cartilage or bone disorder may involve the loss of adhesion of cartilage to appropriate bone surfaces, for example following traumatic cartilage fractures. A cartilage or bone disorder may include a loss of bone or cartilage volume or strength, for example in subjects with osteoporosis or in cartilage insufficiency, cartilage wear or cartilage failure.

The term "pharmaceutically acceptable carrier or diluent" as used herein is intended to encompass not only a carrier or diluent which is suitable for administration to a human subject, but also a carrier or diluent which is suitable for administration to a non-human mammalian subject. In particular embodiments, the carrier or diluent is suitable for administration to a non-human mammalian subject. In particular embodiments the carrier or diluent is suitable for administration to a human subject.

The terms "treating", "treatment", "therapy" and the like in the context of the present specification refer to the alleviation of the symptoms and/or the underlying cause of an inflammatory disorder or a cartilage or bone disorder. In certain embodiments a treatment will slow, delay or halt the progression of a disorder or the symptoms of the disorder, or reverse the progression of the disorder at least temporarily. The "treatment" of an inflammatory disorder in a subject may take place at the time the subject exhibits detectable inflammation associated with the disorder, or before the onset of substantial inflammation. Typical symptoms of acute inflammation include redness and heat due to vasodilation, swelling due to edema, and pain at the site of inflammation and loss of function; however, a definitive diagnosis of inflammation is typically not made on the basis of the presence of absence of one of these symptoms alone. Typically inflammation is associated with leukocyte extravasation and infiltration into tissue.

The "alleviation of pain associated with an inflammatory disorder" is intended to encompass a reduction in pain which results from an inflammatory disorder, but not necessarily treating the inflammatory disorder which causes the pain.

In the context of this specification, the term "comprising" means including but not necessarily solely including. Furthermore, variations of the word "comprising" such as "comprise" and "comprises" have correspondingly varied meanings.

Throughout this specification, reference to "a" or "one" element does not exclude the plural, unless context determines otherwise.

The examples which follow are intended to serve to illustrate this invention and should not be construed as limiting the general nature of the disclosure of the description throughout this specification.

EXAMPLES

Example 1

Preparation of a Mixture of Adipocytes and Adipose-Derived Non-Adipocyte Cells A 10 g sample of adipose tissue was collected by excision from the groin of an adult dog. The adipose tissue was rinsed with saline and then minced finely using scissors and mixed with 20 ml of Dulbecco's Modified Eagle's Medium (DMEM, Sigma). Collagenase (Sigma) was added to achieve a final concentration of 0.05% and the sample was incubated at 37° C. for 90 minutes. During the incubation the sample was gently inverted by hand every 15 minutes.

Following collagenase treatment the sample was aseptically filtered through a stainless steel mesh (300 μm pore size), transferred to a 50 ml centrifuge tube and centrifuged at 500 g for 15 minutes.

Four distinct layers were visible within the centrifuged sample: a small (2 mm thick) layer of free lipid on the surface, below which was a white 10 mm thick layer of adipocytes and then a large clear layer of liquid which largely comprised DMEM and then a pellet of adipose-derived non-adipocyte cells. The small layer of lipid was carefully removed with a pasteur pipette. A fresh pasteur pipette was then carefully inserted through the adipocytes and the clear DMEM was removed without disturbing the floating adipocytes or the pelleted cells. This resulted in a sample that contained only the floating adipocytes and the pelleted cells. The floating adipocytes and the pelleted cells were gently mixed with a pasteur pipette and transferred to a 15 ml centrifuge tube.

The cells were then washed in DMEM to remove collagenase. DMEM was added to a final volume of 14 ml and the sample centrifuged at 500 g for 10 minutes. This resulted in three distinct layers: floating adipocytes, DMEM and pelleted adipose-derived non-adipocyte cells. The DMEM was carefully removed by inserting a pasteur pipette through the adipocytes taking care not to disturb the adipocytes or the pelleted cells.

The floating and the pelleted cells were gently resuspended in 4 ml of DMEM and mixed with a pasteur pipette.

Example 2

Use of a Filter Plunger Device for Preparing a Mixture of Adipocytes and Adipose-Derived Non-Adipocyte Cells A sample of canine adipose tissue was minced and digested as described in Example 1. After the 90 minute incubation at 37° C. the sample was aseptically filtered through a stainless steel mesh (300 μm pore size) and then the filtrate containing isolated adipose tissue-derived cells and small pieces of adipose tissue was transferred to the lower portion of a filter plunger device.

The filter plunger device utilised a centrifuge tube to hold a cell suspension sample, and a plunger with a filter element with a pore size of around 200 μm which was inserted into the tube and forced into the sample to produce pressure sufficient to allow the separation of cells and the medium in which the cells are suspended.

The filter was removed and the filtrate was tipped into a centrifuge tube. The filter was then replaced and the sample was centrifuged at 500 g for 15 minutes. The adipocytes and the adipose-derived non-adipocyte cells were driven to the bottom of the tube by the filter plunger and centrifugal force. The supernatant was tipped off and a further 10 ml of DMEM was added to top of the tube. The sample was centrifuged once again at 500 g for 15 minutes after which the supernatant was tipped off leaving a mixture of adipocytes and adipose tissue-derived non-adipocyte cells.

Example 3

Preparation of a Cell-Free Extract from an Adipose Tissue-Derived Cell Suspension A 10 g sample of canine adipose tissue was minced finely using scissors and then mixed with 5 ml of DMEM. Autologous canine serum was filter sterilised and a 1 ml volume added to the mixture of minced tissue.

The tissue mixture was incubated at 37° C. overnight without agitation. The sample was then centrifuged at 1500 g for 15 minutes and the liquid between the floating layer of adipocytes and the pellet of adipose tissue-derived non-adipocyte cells was carefully harvested.

Example 4

Alternative Preparation of a Cell-Free Extract from an Adipose Tissue-Derived Cell Suspension A 10 g sample of adipose tissue was collected by excision from the groin of a dog. The adipose tissue was rinsed with saline and then minced finely using scissors and mixed with 20 ml of Dulbecco's Modified Eagle's Medium (DMEM, Sigma). Collagenase (Sigma) was added to produce a final concentration of 0.05% and the sample was incubated at 37° C. for 90 minutes, during which time the sample was gently inverted by hand every 15 minutes.

The sample was then aseptically filtered through a stainless steel mesh (300 μm pore size), transferred to a 50 ml centrifuge tube and centrifuged at 500 g for 15 minutes.

Four distinct layers were visible within the centrifuged sample: a small (2 mm thick) layer of free lipid on the surface, below which was a white 10 mm thick layer of adipocytes and then a large clear layer of DMEM and then a pellet of adipose tissue-derived non-adipocyte cells. The small layer of lipid was carefully removed with a pasteur pipette. A fresh pasteur pipette was then carefully inserted through the adipocytes and the clear DMEM was removed without disturbing the floating adipocytes or the pelleted cells. This resulted in a sample that contained only the floating adipocytes suspended in a small volume of DMEM and the pelleted cells. The floating and the pelleted cells were gently mixed with a pasteur pipette and transferred to a 15 ml centrifuge tube.

The cells were then washed in DMEM to remove collagenase as follows. DMEM was added to a final volume of 14 ml and the sample centrifuged at 500 g for 10 minutes. This resulted in three distinct layers: floating adipocytes, DMEM and pelleted adipose-derived non-adipocyte cells. The DMEM was carefully removed by inserting a pasteur pipette through the adipocytes taking care not to disturb the adipocytes or the pelleted cells.

The floating and the pelleted cells were gently resuspended in 4 ml of DMEM plus 1 ml of filter sterilised autologous serum and mixed with a pasteur pipette. The mixture of cells was then incubated at 37° C. overnight with shaking (100 rpm). The sample was then centrifuged at 1500 g for 15 minutes and the liquid between the floating layer and the pellet was carefully harvested. The liquid sample was then filter sterilised.

Example 5

Production of a Mixture of Adipocytes and Adipose-Derived Non-Adipocyte Cells Depleted of Adherent Cells A 4 ml volume of adipocytes and adipose-derived non-adipocyte cells was prepared as described in Example 1.

Autologous canine serum was filter sterilized and a 1 ml volume added to the cell mixture.

The cell mixture was incubated at 37° C. overnight in a tissue culture flask without agitation. The sample was examined using an inverted microscope and a layer of cells adhering to the surface of the flask was observed. Unattached cells and floating adipocytes were also observed. The non-adherent cells, comprising adipocytes and adipose-derived non-adipocyte cells were carefully tipped off and collected. These cells are suitable for direct in vivo use or for the generation of a cell-free extract for in vivo use.

Example 6

Production of a Mixture of Adipocytes and Adipose-Derived Non-Adipocyte Cells Depleted of CD34-Positive Cells A 4 ml volume sample of adipocytes and adipose-derived non-adipocyte cells was prepared as described in Example 1.

Anti-mouse magnetic beads (Dynal, Oslo) were coated with an anti-canine CD34 monoclonal antibody (Becton Dickinson, San Jose, Calif.) according to the bead manufacturer's instructions. A 100 µl aliquot of anti-CD34 beads (approximately $1 \times 10^6$ beads) was added to the cell mixture and incubated at room temperature for 1 hour. The sample was gently inverted every 5 minutes. A magnet was then placed on the side of the tube for 2 minutes and the sample carefully tipped off with the magnet still in place, producing a population of adipocytes and adipose-derived non-adipocyte cells depleted of CD34 positive cells in the supernatant.

The CD34 positive cell-depleted cell suspension is suitable for direct in vivo use or for the generation of a cell-free extract for in vivo use.

Example 7

Preparation of a Suspension of Adipocytes

A 10 g sample of adipose tissue was collected by excision from the groin of a dog. The adipose tissue was rinsed with saline and then minced finely using scissors and mixed with 20 ml of Dulbecco's Modified Eagle's Medium (DMEM, Sigma). Collagenase (Sigma) was added to a final concentration of 0.05% and the sample was incubated at 37° C. for 90 minutes. The sample was gently inverted by hand every 15 minutes.

The sample was then aseptically filtered through a stainless steel mesh (300 µm pore size), transferred to a 50 ml centrifuge tube and centrifuged at 500 g for 15 minutes.

Four distinct layers were visible within the centrifuged sample: a small (2 mm thick) layer of free lipid on the surface, below which was a white 10 mm thick layer of adipocytes and then a large clear layer of DMEM and then a pellet of adipose-derived non-adipocyte cells. The small layer of lipid was carefully removed with a pasteur pipette. A fresh pasteur pipette was then carefully inserted through the adipocytes and the clear DMEM and the pelleted cells were removed. This resulted in a sample that contained only the floating adipocytes. The adipocytes were gently mixed with a pasteur pipette and transferred to a 15 ml centrifuge tube.

The adipocytes were then washed in DMEM to remove collagenase as follows. DMEM was added to a final volume of 14 mls and the sample centrifuged at 500 g for 10 minutes. The DMEM was carefully removed by inserting a pasteur pipette through the adipocytes.

The floating cells, comprising adipocytes, were gently resuspended in 4 mls of DMEM.

Example 8

Treating Canine Arthritis with a Cell-Free Extract

A 4 year old German Shepherd was diagnosed with severe acute arthritis in the right hip and stifle was recruited for studies with a cell-free extract. The dog had a history of cruciate ligament rupture followed by surgical repair of the cruciate. The dog was previously treated with the non-steroidal anti-inflammatory meloxicam for 4 weeks and showed no improvement in mobility or willingness to be active. It was concluded that the arthritis was likely to degenerate further.

A second dog, a 10 year old Golden Retriever with degenerative joint disease was also recruited for studies with a cell-free extract. The dog had showed symptoms of arthritis for 5 years and over that time had been treated with non-steroidal anti-inflammatory agents cartrophen, carprophen and meloxicam. None of these treatments resulted in significant improvement in the animal and the rate of degeneration was accelerating.

Treatment with a cell-free extract was performed on each animal. Fat (6 grams from the German Shepherd and 14 grams from the Golden Retriever) was excised from is the anaesthetised animals and processed as detailed in Example 3 to generate cell free extracts. On the day after excision of fat tissue, 1.5 ml of the cell free extract was injected into each of the right hip and stifle of the German shepherd and 1.5 ml of the cell free extract was injected into all eight joints of the golden Retriever.

The owners were asked to complete a questionnaire on the lameness and mobility of the dog before the treatment and 10 days and 1 month after the treatment. The questionnaire used a horizontal line 100 mm in length as a "visual analogue scale". Each end of the line had word descriptors. A score was determined by measuring in millimeters from the left hand end of the line to the point that the owner marked. This approach has been demonstrated to provide most value when looking at changes within individuals (Crichton, N. (2001) Visual Analogue Scale (VAS) In: Blackwell Science Ltd, Journal of Clinical Nursing). An assessment of each animal by the attending vet was also made at the same time period. The text of the owner questionnaire is presented as follows:

Owner Questionnaire

Please read the following instructions

Reply to each question by placing a vertical mark on the corresponding line.

When assessing your dog over the past day, week or month mark down your dog's usual behaviour The following is a definition of lameness: Disabled so that movement is difficult or impossible 1. Rate your dog's willingness to play voluntarily Very willing                                                   Not at all

0%                                50%                          100%

2. Rate how much voluntary exercise your dog gets

Frequent amounts                                       None

0%                                50%                          100%

3. Rate how often your dog gets exercise

Very often                                                 Never

0%                                50%                          100%

4. Rate how easy is it for your dog to get into the vehicle or jump on to furniture Very easy                                       Extremely difficult

0%                                50%                          100%

5. Rate your dog's ease in lying down

Very easy                                       Extremely difficult

0%                                50%                          100%

6. Rate your dog's ease in sitting on his/her haunches

Very easy                                       Extremely difficult

0%                                50%                          100%

-continued

7. Rate your dog's ease to rise from a lying position
   Very easy                              Extremely difficult
   0%               50%               100%
8. Rate your dog's ease of movement after a long rest
   Very easy                              Extremely difficult
   0%               50%               100%
9. Rate your dog's ease in rising from a sitting position
   Very easy                              Extremely difficult
   0%               50%               100%
10. Rate how easy it is for your dog to lift his leg to urinate
    Very easy                             Extremely difficult
    0%               50%               100%
11. Rate how easy it is for your dog to squat to urinate/defecate
    Very easy                             Extremely difficult
    0%               50%               100%
12. Rate how willingly your dog walks up stairs
    Very willing                          Does not climb stairs
    0%               50%               100%
13. Rate how willingly your dog walks downstairs
    Very willing                          Does not descend stairs
    0%               50%               100%
Does your dog vocally indicate pain when touched?
    Never vocalises                       Always vocalises
    0%               50%               100%
15. Rate how stiff your dog is when arising for the day
    Not stiff                             Could not be more stiff
    0%               50%               100%
16. Rate how stiff your dog is at the end of the day
    Not stiff                             Could not be more stiff
    0%               50%               100%
17. Does your dog indicate any lameness at a walk?
    Rarely                                Always
    0%               50%               100%
18. Does your dog indicate any lameness at a trot?
    Rarely                                Always
    0%               50%               100%
19. Does your dog indicate any lameness at a run?
    Rarely                                Always
    0%               50%               100%
20. Rate your dog's pain (if any) when turning suddenly at play
    No pain                               Extremely painful
    0%               50%               100%

Total % scores were obtained from each questionnaire and an average score for an individual animal obtained by dividing the % total score by the number of questions (20). A lower average score indicated an animal exhibiting fewer signs of limited mobility as assessed by the animal's owner.

TABLE 1

Average Clinical score over time as measured by owner questionnaire

| Animal | Pre-treatment | 10 days post treatment | 1 month post treatment |
|---|---|---|---|
| German Shepherd | 27 | 12 | 3.5 |
| Golden Retriever | 31 | 22 | — |

An orthopaedic examination was performed on the Golden Retriever by a veterinarian before the treatment and 10 days after the treatment. The veterinarian scored the orthopaedic condition of the animal according to the scale listed below.
Veterinary Completed Orthopaedic Examination

| Lame at walk | Lame at trot |
|---|---|
| 0 not detectable | 0 not detectable |
| 1 intermittent | 1 intermittent |
| 2 persistent | 2 persistent |
| 3 ambulatory with assistance | 3 ambulatory with assistance |
| 4 non-ambulatory | 4 non-ambulatory |

| Lame at run | Range of motion, flexion and extension (including goniometry) |
|---|---|
| 0 not detectable | 0 no limitation |
| 1 intermittent | 1 pain only at full |
| 2 persistent | 2 pain at half |
| 3 ambulatory with assistance | 3 pain at less than half |
| 4 non-ambulatory | 4 pain at any attempt |

| Functional disability | Crepitus |
|---|---|
| 0 normal activity | 0 no crepitus |
| 1 slightly stiff gait, pacing | 1 mild crepitus |
| 2 stiff gait, clearly does not move freely | 2 moderate crepitus |
| 3 very stiff gait, avoids weight bearing on affected limb | 3 audible crepitus |
| 4 does not want to walk | 4 extreme crepitus |

The values from the questionnaire were averaged and are shown in Table 2.

TABLE 2

Average Clinical score over time assessed by veterinarian.

| Animal | Pre-treatment | 10 days post treatment |
|---|---|---|
| Golden Retriever | 1.1 | 0.1 |

These results demonstrate a marked improvement in both animals with an almost complete recovery within 1 month for the German Shepherd diagnosed with severe acute arthritis, and a rapid improvement in symptoms of the Golden Retriever. Both animals had chronic and progressive disease, and were not responding to usual non-steroidal anti-inflammatory agent treatments.

This rapid and marked improvement, and the sustaining of the improvement exhibited over the longest period examined (one month) suggests not only that the cell-free extract produced a rapid reduction in pain stimuli arising from the affected joints, but also that this reduction in painful stimuli was maintained for a period of weeks at least. The sustained maintenance of recovery over a period of at least one month suggests that the therapeutic intervention produced more than a mere analgesic response.

Example 9

Treating Canine Arthritis with an Autologous Mixture of Adipocytes and Adipose-Derived Non-Adipocyte Cells Twenty six dogs with arthritis were recruited for studies using an autologous mixture of adipocytes and adipose-derived non-adipocyte cells.

Each of the dogs had been showing degenerative joint disease for 12 months. During the 12 months the dogs had been treated with cartrophen, carprophen and meloxicam. None of the treatments resulted in noticeable improvement in the animals and the rate of degeneration was accelerating.

Fat (12 to 16 grams) was excised from each of the anaesthetised animals and processed individually as detailed in Example 1. A 1.5 ml volume of the resultant cell mixture of autologous adipocytes and adipose-derived non-adipocyte cells was injected into the affected joints of the dogs.

A questionnaire (described in Example 8) was completed by each of the owners before treatment, at 10 days after treatment (10 d) and then monthly at 1 to 6 months after treatment (m 1 to m 6). The averaged results are presented in Table 3.

An orthopaedic examination was performed by a veterinarian before the treatment 10 days after the treatment, and on monthly follow up. The veterinarian scored the orthopaedic condition of the animal according to the scale described in Example 8. The scores were averaged and are given in Table 4.

TABLE 3

Clinical score over time as measured by owner questionnaire

| | Pre-Treatment | 10 d | 1 m | 2 m | 3 m | 4 m | 5 m | 6 m |
|---|---|---|---|---|---|---|---|---|
| Willingness to play voluntarily | 51 | 29 | 31 | 26 | 28 | 29 | 33 | 35 |
| How much voluntary exercise | 50 | 39 | 36 | 37 | 37 | 40 | 37 | 32 |
| How often dog exercises | 43 | 35 | 32 | 28 | 34 | 34 | 33 | 32 |
| Ease of jumping into vehicle/furniture | 67 | 51 | 41 | 41 | 42 | 42 | 43 | 42 |
| Ease in lying down | 51 | 32 | 28 | 19 | 28 | 25 | 28 | 26 |
| Ease in sitting on haunches | 53 | 36 | 32 | 28 | 31 | 31 | 31 | 29 |
| Ease in rising from a lying position | 59 | 37 | 29 | 26 | 29 | 33 | 33 | 32 |
| Ease of movement after a long rest | 61 | 39 | 32 | 29 | 35 | 33 | 35 | 31 |
| Ease of rising from a sitting position | 56 | 33 | 28 | 21 | 29 | 28 | 31 | 30 |
| Ease of squatting to urinate/defecate | 41 | 28 | 22 | 16 | 22 | 21 | 20 | 22 |
| Willingness to walk upstairs | 51 | 32 | 24 | 22 | 27 | 30 | 33 | 26 |
| Willingness to walk downstairs | 52 | 31 | 27 | 26 | 29 | 29 | 30 | 27 |
| Vocal indication of pain when touched | 32 | 24 | 28 | 29 | 23 | 32 | 31 | 25 |
| Stiffness when arising for the day | 54 | 35 | 28 | 28 | 29 | 28 | 29 | 29 |
| Stiffness at the end of the day | 48 | 34 | 25 | 21 | 22 | 24 | 22 | 28 |
| Lameness at walk | 56 | 34 | 33 | 29 | 32 | 30 | 37 | 35 |
| Lameness at trot | 58 | 40 | 32 | 29 | 33 | 31 | 37 | 31 |
| Lameness at run | 57 | 49 | 40 | 30 | 31 | 28 | 38 | 34 |
| Pain when turning suddenly at play | 54 | 38 | 27 | 25 | 22 | 25 | 27 | 22 |
| AVERAGE | 52 | 36 | 30 | 27 | 30 | 30 | 32 | 30 |

TABLE 4

Clinical score over time assessed by veterinarian.

| | Pre-treatment | 10 d | 1 m | 2 m | 3 m | 4 m | 5 m | 6 m |
|---|---|---|---|---|---|---|---|---|
| Lame at walk | 1.4 | 0.8 | 0.5 | 0.5 | 0.4 | 0.5 | 0.6 | 0.6 |
| Lame at trot | 1.4 | 0.8 | 0.7 | 0.5 | 0.4 | 0.4 | 0.6 | 0.6 |
| Lame at Run | 1.4 | 0.8 | 0.7 | 0.5 | 0.4 | 0.3 | 0.6 | 0.5 |
| Range of motion | 2.3 | 1.3 | 1.0 | 1.4 | 0.8 | 1.1 | 1.1 | 0.8 |
| Functional disability | 2.0 | 0.9 | 0.5 | 0.5 | 0.7 | 0.5 | 0.9 | 0.8 |
| Crepitus | 1.9 | 1.2 | 0.9 | 1.0 | 0.9 | 0.9 | 1.0 | 0.8 |
| Swelling | 1.1 | 0.6 | 0.3 | 0.6 | 0.3 | 0.3 | 0.3 | 0.2 |
| Jumping (Into vehicle) | 2.7 | 2.2 | 1.8 | 1.7 | 1.2 | 1.2 | 1.2 | 1.4 |
| Stairs | 2.1 | 1.0 | 0.7 | 0.7 | 0.6 | 0.8 | 0.7 | 0.7 |
| Proprioception | 0.6 | 0.2 | 0.1 | 0.0 | 0.0 | 0.1 | 0.1 | 0.0 |
| Pain on Manipulation | 2.0 | 1.1 | 0.8 | 0.8 | 0.6 | 0.6 | 0.6 | 0.4 |
| AVERAGE | 1.7 | 1.0 | 0.7 | 0.8 | 0.6 | 0.6 | 0.7 | 0.6 |

These results demonstrate a marked improvement in the animals within only 10 days. The improvement is maintained for at least six months.

Example 10

Treatment of Canine Skin Inflammation by Intradermal Injection of an Allogeneic Cell-Free Extract Prepared from an Adipose Tissue-Derived Cell Suspension A 10 g sample of adipose tissue was collected from the falciform ligament from a female dog during a routine desexing procedure. An extract was prepared from the adipose tissue as described below and this extract was used to treat an allergic inflammatory skin reaction in another, unrelated dog.

The 10 g sample of adipose tissue was aseptically minced using scissors and then mixed with 10 ml of DMEM. A 2 ml volume of filter sterilised canine serum was added to the mixture of minced tissue. Sterile cephazolin was added to a final concentration of 20 mg per ml. The suspended tissue mixture was incubated at 37° C. overnight with gentle agitation, after which suspended tissue mixture was centrifuged at 1500 g for 15 minutes. Following centrifugation the cell free "extract" between the floating layer of adipocytes and lipid and the cell pellet was carefully harvested, filter sterilised and stored frozen in is 2 ml aliquots.

A Beagle-cross dog presented with an allergic inflammatory skin reaction. The atopy was associated with severe pruritis, skin reddening and matted fur due to the dog licking. Previously this subject had been successfully treated for pruritic skin two years ago using corticosteroids. This treatment option was no longer available as the dog now had Cushing's disease, which prevented steroids being used. The atopy was recent, severe, self traumatising and unlikely to spontaneously resolve.

A 2 ml volume of the adipose tissue extract was thawed and taken up into a syringe fitted with a 28 gauge needle. The adipose tissue extract was injected intradermally at multiple sites across the area of inflammation. No other treatment was given to the dog.

The animal was examined at 2 days post treatment and the area of inflammation was dry, much less swollen and no longer pruritic. A second examination was performed at 5 days post treatment and the area appeared completely healed.

Example 11

Treatment of Skin Inflammation in a Canine by Topical Application of an Allogenic Cell-Free Extract Prepared from an Adipose Tissue-Derived Cell Suspension A 7 year old Rhodesian Ridgeback with apparent immune-mediated skin inflammation around the arm pits and abdomen was treated with a topical application of an adipose tissue extract.

A 5 ml volume of allogeneic adipose tissue cell free extract previously described in Example 10 was thawed and mixed with Aqueous Cream BP at a ratio of 1:1. This mixture was applied to the area of inflammation twice daily for 3 days.

At 1 day post treatment the inflammation was markedly reduced and the dog was no longer scratching the affected areas. At 3 days post treatment the inflammation was completely gone and the skin appeared healed.

Example 12

Treatment of a Corneal Ulcer in a Canine with an Autologous Cell-Free Extract Prepared from an Adipose Tissue-Derived Cell Suspension

A dog with a corneal ulcer was treated with an autologous adipose tissue cell free extract which was prepared along the lines of the methods described in Example 10.

A fifteen year West Highland white terrier dog presented with an upper eyelid tumour of approximately 25% of the width of the lid diameter. The tumour was surgically removed and the defect replaced by an advancement flap.

The eyelid sutures resulted in post surgical irritation of the eye, and a large superficial ulcer developed on the dorsocaudal aspect of the eye, directly under the suture knot. This was associated with vascular ingrowths in the cornea and conjunctivitis. The ulcer deteriorated into a progressing chronic ulcer which was associated with marked inflammation. Although the dog was being treated with oral antibiotics, an eye lubricant/bacteriostatic and an oral non-steroidal anti-inflammatory drug, the ulcer did not respond to this treatment and continued to expand in area and into deeper layers of the cornea.

A grid keratectomy was then performed on the ulcer using a needle, and the treatment described above maintained. The inflammation continued to worsen, with marked vascular ingrowths in the 10 to 2 o'clock position and ongoing ulceration.

A sample of approximately 10 grams of adipose tissue was extracted from the inguinal fat pad this dog and processed as detailed in Example 10. The resultant cell-free extract prepared from an adipose tissue-derived cell suspension was applied to both of the dog's corneas 4 times per day, using a sterile plastic pipette. A corneal lubricant/bacteriostatic was applied to the ulcerated eye 1 hour after the application of the tissue extract, but only applied twice daily.

After 48 hours from the first application of the cell-free extract the corneal inflammation appeared markedly less aggressive and more diffuse, and the ulcer had shrunken in area by approximately 75% as evidenced by flourescein staining of the corneal surface.

At 96 hours after commencement of treatment the corneal ulcer had completely sealed over with corneal epithelium with evidence of the formation of early scar tissue and gross generalised neovascularisation development in all regions within the cornea. The vasculature was so extensive that there were concerns that eyesight may be affected. Triamcinolone acetonide corticosteroid ointment was applied in an ongoing manner for up to three months to reduce the vasculature. Treatment continued for 10 days with the cell-free extract, the eye lubrication and the antibiotic.

At 7 days post treatment the inflammation was no longer present and the ulcer was fully sealed and healing well, and by 14 days post treatment the ulcer was fully healed.

Example 13

Treatment of a Corneal Ulcer in a Canine with an Allogeneic Cell-Free Extract Prepared from an Adipose Tissue-Derived Cell Suspension

An eight year old Lhasa Apso dog presented with a paralysed eye lid. A paralysis tick was removed from above the dog's eye. Paralysis ticks are a common cause of temporary paralysis of the eye lid in animals. The dog subsequently developed dry eye, which then deteriorated into a corneal ulcer.

The ulcer was initially treated with chloramphenicol, artificial tears and an ocular lubrication eye ointment for two days; however, the ulcer continued to deteriorate.

The adipose tissue extract as detailed in Example 10 and an additional adipose tissue extract prepared using the method described in Example 10 from another donor canine was applied to the cornea (3 drops of approximately 0.2 ml each) every 4 hours for 3 days. The chloramphenicol, artificial tears and lubrication eye ointment were also applied two hours after each application of the adipose tissue extract.

After 3 days the eye lid remained paralysed but the ulcer had reduced in size by 50%. After 10 days the eye lid paralysis had resolved naturally and the ulcer continued healing.

Example 14

The Use of a Mixture of Autologous Adipocytes and Adipose-Derived Non-Adipocyte Cells as a Compliment to Orthopaedic Surgery

Nine canines which were subject to types of orthopaedic surgery which are known to result in osteoarthritis were treated with a mixture of autologous adipocytes and other adipose derived cells, prepared as described below.

Each dog was anesthetized and a 10 g sample of adipose tissue was collected by excision from the groin. The adipose tissue from each dog was separately rinsed with saline and digested as described in Example 1 to prepare mixture of autologous adipocytes and adipose-derived non-adipocyte cells.

Six dogs (a 5 year old Bull dog, a 5 year old Labrador, a 12 year old Labrador, a 9 year old Ridgeback, a 7 year old cattle dog, and a 2 year old Newfoundland) were treated at the time of performing anterior cruciate ligament repair. A 1.5 ml volume of autologous cell preparation was injected directly into the relevant joint capsule of each dog.

Two dogs with osteochondritis dissecans (OCD) were treated with autologous adipocytes and adipose-derived non-adipocyte cells. A two year old border collie had large OCD lesions removed from both tarsi. A nine year old Brittany spaniel had OCD lesions removed from bilateral shoulders. Both dogs had 1.5 ml of autologous cell preparation injected directly into the joint either at the time of surgery or on the same day but some hours after surgery with correct needle placement identified by the extraction of synovial fluid. The expected post-operative discomfort and swelling associated with this procedure as assessed by the veterinary surgeon using standard orthopaedic veterinary examination techniques was not evident in either dog.

One dog, a Maltese terrier, received 1.5 ml of autologous adipocytes and adipose-derived non-adipocyte cells into the stifle joint, at the same time as a tibial crest transplant to treat bilateral luxating patellas.

All of these dogs were perceived by the veterinarian to have an improved recovery time, with less post-operative complication. The reduction of complications suggests that these animals are less likely to subsequently develop osteoarthritis.

Example 15

The Treatment of Osteoarthritis in a Feline Using a Mixture of Allogeneic Adipocytes and Adipose-Derived Non-Adipocyte Cells

An adult male Burmese cat acted as a donor for the recipient subject, an eleven year old domestic shorthaired cat, for the treatment of osteoarthritis. The veterinary history of the recipient detailed osteoarthritis for two years prior to treatment. Adipose tissue (13.5 g) was retrieved from the inguinal fat pads of the donor cat, and processed as described in Example 1 to generate a cell suspension. Approximately 1,971,000 cells were collected for injection. A 1 ml volume of the cellular suspension was injected into both of the recipient cat's elbows with a 23 gauge needle.

An improvement in osteoarthritis was noted by the veterinarian and the animal's owner, as evidenced by improvements in mobility. The recipient cat, for example, had been unable to walk up or down stairs prior to the procedure, but was able to do so after the procedure. Although an allogeneic cell suspension was used for this treatment, there was no evidence that the recipient cat experienced immune rejection of the allogeneic tissue, as assessed by the recipient's vital signs following surgery.

Example 16

Treatment of Canine Degenerative Myelopathy with a Mixture of Autologous Adipocytes and Adipose-Derived Non-Adipocyte Cells A 10 year old German Shepherd dog with degenerative myelopathy had progressed to the point where the owners were ready to euthanize the animal. The animal was not able to walk and had to be carried into the veterinary hospital.

The animal was treated with an autologous preparation of adipocytes and adipose derived cells which was prepared using the method described in Example 1. 10.3 grams of fat was collected from the inguinal fat pad of the subject, and approximately 1.8 million cells in total in a 1 ml volume were collected from this tissue for use. The cells were injected under x-ray guidance into the epidural space.

At one month post-treatment the animal was significantly more mobile as assessed visually and using standard orthopaedic veterinary examination techniques, and the condition of the animal had improved sufficiently that the owners were no longer considering euthanasia. Remission in this condition is unusual and is not expected spontaneously.

Example 17

Treatment of Canine Rheumatoid Arthritis with a Mixture of Autologous Adipocytes and Adipose-Derived Non-Adipocyte Cells A 3 year old Golden Retriever presented with rheumatoid arthritis and mild hip dysplasia. This condition was assessed as being continuous and progressive. The animal was treated with an autologous mixture of adipocytes and adipose-derived non-adipocyte cells which was prepared using the method described in Example 1. A volume of 3 ml of cell suspension containing a total of approximately 2.547 million cells was divided and injected into both hip joints (1.5 ml/joint).

At 2 weeks post treatment the animal was significantly improved as assessed by the owners. Lameness and activity levels were all dramatically improved, as detailed in the answers to owner-completed questionnaire (as described in Example 8) set out below in Table 5.

TABLE 5

Clinical score over time as measured by owner questionnaire

| Owner completed questions | Pre-operation | 10 days post | 1 month post | 2 months post |
|---|---|---|---|---|
| Willingness to play voluntarily | 99 | 3 | 5 | 0 |
| How much voluntary exercise | 99 | 34 | 4 | 0 |
| How often dog exercises | 99 | 31 | 3 | 0 |
| Ease of jumping into vehicle/furniture | 99 | 0 | 2 | 0 |
| Ease in lying down | 50 | 0 | 2 | 0 |

TABLE 5-continued

Clinical score over time as measured by owner questionnaire

| Owner completed questions | Pre-operation | 10 days post | 1 month post | 2 months post |
|---|---|---|---|---|
| Ease in sitting on haunches | 80 | 8 | 5 | 0 |
| Ease in rising from a lying position | 99 | 9 | 1 | 0 |
| Ease of movement after a long rest | 99 | 10 | 1 | 0 |
| Ease of rising from a sitting position | 86 | 4 | 1 | 0 |
| Ease of squatting to urinate/defecate | 77 | 0 | 2 | 0 |
| Willingness to walk upstairs | 92 | 0 | 0 | 0 |
| Willingness to walk downstairs | 91 | 0 | 0 | 0 |
| Vocal indication of pain when touched | 2 | 0 | 0 | 0 |
| Stiffness when arising for the day | 94 | 0 | 0 | 0 |
| Stiffness at the end of the day | 95 | 6 | 0 | 0 |
| Lameness at walk | 92 | 0 | 0 | 0 |
| Lameness at trot | 90 | 0 | 0 | 0 |
| Lameness at run | 96 | 0 | 0 | 0 |
| Pain when turning suddenly at play | 97 | 0 | 0 | 0 |

Example 18

Treatment of Osteoarthritis in a Canine with an Allogeneic Cell-Free Free Extract Prepared from an Adipose Tissue-Derived Cell Suspension A 13 year old German Shepherd presented with osteoarthritis of the hips and stifles. The animal was treated with an allogeneic adipose tissue cell-free extract prepared using the methods as detailed in Example 10. The extract (8 ml in total) was injected into both hip and stifle joints (2 ml per joint).

There was no negative response due to injection of the allogeneic material. At 2 weeks after treatment the animal appeared less lame as assessed by the veterinarian.

Human Therapy

Example 19

Treatment of a Human Subject with Osteoarthritis with an Autologous Adipose Tissue-Derived Cell Suspension A 64 year old female subject with osteoarthritis of the left knee provided informed consent for treatment. MRI imaging of the right knee showed extensive osteoarthritic change in patello-femoral and medial compartment of the knee, in particular with degenerate knee menisci and short radial tears, particularly involving the lateral meniscus. There was mild synovial perforation related to rheumatoid, although overall, the MRI suggested that the oseoarthritic change would outweigh the effects of rheumatoid.

Examination of the knee by a radiologist reported osteoarthritic changes in the knee joint with medial joint compartment narrowing and osteophyte formation of the articular margins and there were further degenerative changes at the patello-femoral joint. No joint effusion or other intra-articular abnormality was detected, nor were any fracture or signs of acute injury detected.

Previous treatment involved medication including non-steroidal anti-inflammatory agents, pain-killers and physiotherapy. The subject had been hospitalised twice due to extensive swelling of the knee.

An adipose tissue-derived cell suspension comprising adipocytes was prepared according to the following protocol.

A lipoaspirate sample was retrieved from the abdomen of the subject using standard liposuction procedures. Thirty ml of lipoaspirate and tumescent fluid (1 liter of sodium chloride plus 1 ml of 8.4% sodium bicarbonate and 1 ml of 1:1000 adrenalin and 40 mg of lignocaine) were placed upright in 50 ml syringes under sterile conditions. The fat and tumescent were separated, with the tumescent transferred into one 50 ml sterile centrifuge as tube and the fat transferred into 50 ml sterile centrifuge tubes containing collagenase in a sterile solution containing 0.45% sodium chloride and 2.5% glucose. The fat sample was digested at 37° C. for 45 minutes, during which time the tubes were inverted every 10 minutes.

The centrifuge tubes digest were then centrifuged at 400 g at room temp for 10 minutes, and the layer between the floating adipocytes and the pelleted cells was removed. The cell pellet and floating adipocytes were combined and transferred into three 15 ml sterile centrifuge tubes which contained a sterile solution of 0.45% sodium chloride and 2.5% glucose and filter sterilized autologous serum and the samples were centrifuged at 400 g for 10 minutes at room temp.

The layer between the pelleted cells and the floating adipocytes was removed, and the combined cell preparation was diluted to a volume of 9 ml with a sterile solution of 0.45% sodium chloride and 2.5% glucose. An aggregate formed in the sample whilst mixing the sample gently, and this was removed. The final volume of the sample was 8 ml, and this contained approximately 20 million cells with 90% viability.

The subject was administered by applying a local anaesthetic to the knee and then inserting a 23 gauge needle into the joint space and injecting the cells.

The subject was asked to describe the pain she experienced on a scale of 0 to 10, with a 0 meaning no pain and a 10 meaning worst possible pain. The subject described child birth as a 10, the pain following a hysterectomy as an 8 and the pain she experienced in her knee ranging from 2.5 to 8.

Seven days prior to treatment she describes the pain in her knee as 8. The day of treatment she described her pain as 2.5 prior to the treatment.

On the day following surgery (Day 1) the subject noted pain in the abdomen from where the lipoaspirate was taken. Her knee felt tight but not painful. There was no unusual sensation in her knee, or bruising over the treated knee. The subject had taken oral paracetamol, but she advised that this was principally because she had a cold and sore throat, and not due to pain.

On Day 2 the subjects abdomen was not painful, and only slightly sore at the incision site. The subject noted that the pain in her knee she normally experienced in the mornings and while showering was absent, although the subject was not sure if this was due to the treatment or because she has been relatively inactive. The subject continued to take oral paracetamol for her cold and sore throat.

By Day 3 the subject's abdomen had recovered considerably. The subject had spent the day shopping. Typically after being on her feet all day the subject's knees and ankles would be swollen, but following the procedure she had no swelling. The subject's right wrist continued to remain un-swollen. When asked to describe the pain in her knee, the subject said she had no pain. The subject was not taking any non-steroidal anti-inflammatory medication, but continued to take oral paracetamol for her cold.

On Day 4 the subject continued to report no pain in her knee. She experienced some pain in her right arm and hand following shopping on day 3. The subject still could not bend down to pick things up, or bend down on her knees, as she continued to experience pain when attempting this.

On follow up between Days 11 to 120 (the latest date examined so far) the subject continued to report no pain in her knee.

What is claimed is:

1. A method for treating an inflammatory disorder or a cartilage disorder or alleviating pain associated with an inflammatory disorder in a subject, comprising the step of administering to the subject a pharmaceutical composition comprising a cell free extract prepared from an adipose tissue-derived cell suspension comprising adipocytes and adipose-derived non-adipocyte cells.

2. The method according to claim 1, wherein the adipose tissue-derived cell suspension is freshly isolated.

3. The method according to claim 1, wherein the adipose tissue-derived cell suspension is autologous to the subject.

4. The method use according to claim 1, wherein the adipose tissue-derived cell suspension is allogeneic to the subject.

5. The method according to claim 1, wherein the subject is a human.

6. The method according to claim 1, wherein the pharmaceutical composition is a veterinary composition and the subject is a non-human mammal.

7. The method according to claim 1, wherein the inflammatory disorder is selected from a joint-related inflammatory disorder, corneal inflammation, or skin inflammation.

* * * * *